US008853277B2

(12) United States Patent
Linehan et al.

(10) Patent No.: US 8,853,277 B2
(45) Date of Patent: Oct. 7, 2014

(54) NITROXIDE THERAPY FOR THE TREATMENT OF VON HIPPEL—LINDAU DISEASE (VHL) AND RENAL CLEAR CELL CARCINOMA (RCC)

(75) Inventors: W. Marston Linehan, North Bethesda, MD (US); Tracey A. Rouault, North Bethesda, MD (US); James Mitchell, Damascus, MD (US); Murali K. Cherukuri, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 206 days.

(21) Appl. No.: 13/512,665

(22) PCT Filed: Nov. 30, 2010

(86) PCT No.: PCT/US2010/058332
§ 371 (c)(1),
(2), (4) Date: Aug. 7, 2012

(87) PCT Pub. No.: WO2011/066537
PCT Pub. Date: Jun. 3, 2011

(65) Prior Publication Data
US 2012/0295937 A1    Nov. 22, 2012

Related U.S. Application Data

(60) Provisional application No. 61/265,194, filed on Nov. 30, 2009.

(51) Int. Cl.
*A61K 31/13* (2006.01)
*A61K 31/40* (2006.01)
*A61K 31/445* (2006.01)
*A61K 31/421* (2006.01)

(52) U.S. Cl.
CPC .............. *A61K 31/40* (2013.01); *A61K 31/445* (2013.01); *A61K 31/421* (2013.01)
USPC ........................................................ 514/645

(58) Field of Classification Search
CPC ........................... A61K 31/40; A61K 31/445
USPC ........................................................ 514/645
See application file for complete search history.

(56) References Cited

U.S. PATENT DOCUMENTS

| 2,868,691 | A | 1/1959 | Porush et al. |
| 3,095,355 | A | 6/1963 | Abramson et al. |
| 5,840,734 | A | 11/1998 | Bernstein |
| 6,605,619 | B1 | 8/2003 | Mitchell et al. |
| 7,074,807 | B2 | 7/2006 | Kasid et al. |

FOREIGN PATENT DOCUMENTS

| WO | WO 96/40127 A1 | 12/1996 |
| WO | WO 98/53835 A1 | 12/1998 |
| WO | WO 2006/084197 A2 | 8/2006 |
| WO | WO 2007/092741 A2 | 8/2007 |
| WO | WO 2008/109740 A2 | 9/2008 |
| WO | WO 2009/152453 A2 | 12/2009 |
| WO | WO 2010/121177 A2 | 10/2010 |

OTHER PUBLICATIONS

Costa LJ, Drabkin Ha. Renal cell carcinoma: new developments in molecular biology and potential for targeted therapies. Oncologist. Dec. 2007;12(12):1404-15.*
DeMarco Vg, Habibi J, Whaley-Connell At, Schneider Ri, Heller Rl, Bosanquet Jp, Hayden Mr, Delcour K, Cooper Sa, Andresen Bt, Sowers Jr, Dellsperger Kc. Oxidative stress contributes to pulmonary hypertension in the transgenic (mRen2)27 rat. Am J Physiol Heart Circ Physiol. Jun. 2008;294(6):H2659-68.Epub Apr. 18, 2008.*
Barlow et al., *Cell* (86), 159-171 (1996).
dE Klein et al., *Nature*, 300, 765-767 (1982).
Donehower, *Semin. Cancer Biol.*, 7(5), 269-278 (1996).
Gariboldi et al., *Eur. J. Cancer*, 39, 829-837 (2003).
Gariboldi et al., *Free Radic. Biol. Med.*, 24(6), 913-923 (1998).
Giovagnoni et al., *Cancer Imaging*, 5: 73-77 (2005).
Hahn et al., *Cancer Research*, 52: 1750-1753 (1992).
Hall, www.fwhc.org, "There Is No Cure for Cancer," (2002).
Harris, *J. Natl. Cancer Inst.*, 88(20), 1442-1455 (1996).
Hollstein et al., *Science*, 253(5015), 49-53 (1991).
Jackson et al., *EMBO J*, 8(2), 449-456 (1989).
Jax Mice Data Sheet, http://jaxmice.jax.org/strain/000664.html (2006).
Jonveaux et al., *Cancer Genet. Cytogenet.*, 66(2), 128-129 (1993).
Kadin et al., *Curr. Opin. Oncol.*, 6(5), 456-463 (1994).
Karmeli et al., *Gut*, 37: 386-393 (1995).
Krishna et al., *J. Biol. Chem.*, 271(42), 26026-26031 (1996).
Krishna et al., *J. Med. Chem.*,41(18), 3477-3492 (1998).
Krishna et al., *Proc. Natl. Acad. Sci. U.S.A.*, 89(12), 5537-5541 (1992).
Li-Fraumeni Syndrome—Genetics Home Reference—definition http://ghr.nlm.nih.gov/condition=lifraumenisyndrome (3 pgs).
Mamet et al., *Biochem. Med. Metab. Biol.*, 52(1), 53-57 (1994).
Marchione et al., www.ledger-enquirer.com, "Drugs Hold Promise in Kidney Cancer Fight," (2006).
Matloff, Reuters News, "Genetic Testing on Embryos Hits New Milestone," http://csweb03.cancersource.com/NewsFeatures/News/detail.cfm?DiseaseID=1&ContentID=22695#Views (2001).
Mitchell et al., *Biochemistry*, 29(11), 2802 (1990).
Mitchell et al., *Free Rad. Biol. Med.*, 34(1), 93-102 (2003).
Monti et al., *J. Cell Biochem.*, 82(2), 271-276 (2001).
Monti et al., *PAACR Annual Meeting*, 36 (#2304), 387 (1995).
Monti et al., *PAACR Annual Meeting*, 38 (#1298), 193 (1997).

(Continued)

*Primary Examiner* — Paul Zarek
(74) *Attorney, Agent, or Firm* — Leydig, Voit & Mayer, Ltd.

(57) ABSTRACT

The invention provides therapeutic methods that include administering a stable nitroxide to a subject that has, is suspected to have, or is at risk for having a condition associated with reduced VHL or elevated HIF-2α.

36 Claims, 1 Drawing Sheet

(56) References Cited

OTHER PUBLICATIONS

Monti et al., *PAACR Annual Meeting*, 39 (#610), 90 (1998).
National Cancer Institute, www.cancer.gov, "Non-Small Cell Lung Cancer: Treatment Patient Version," (2006).
National Cancer Institute, www.cancer.gov "Non-Small Cell Lung Cancer (PDQ®): Treatment Patient Version," (2006).
National Cancer Institute, www.cancer.gov, "Prostate Cancer: Treatment," (2006).
Ninds Ataxia Telangiectasia Information Page, The National institute of Neurological Disorders and Stroke, NIH, http://www.ninds.nih.gov/disorders/a t/a-t.htm (2003).
Prasad et al., *Nutrition*, 14(2): 197-210 (1998).
Purpurra et al., "Adjunctive Treatment of Murine Neuroblastoma with 6-Hydroxydopamine and Tempol," *Cancer Research*, 56: 2336-2342 (1996).
Samuni et al., *J. Biol. Chem.*, 263(34), 17921-17924 (1988).
Schubert et al., *Hum. Molec. Genet.*, 13(16), 1793-1802 (2004).
Simone, Oncology: Introduction, Cecil Textbook of Medicine, 20$^{th}$ Edition, 1, 1004-1010 (1996).
Sutton, April, Baylor College of Medicine, "Baylor, St. Luke's Study Uses Gene Therapy as Pancreatic Cancer," www.bcm.edu (2006).
Suy et al., *Cancer*, 103(6), 1302-1313 (2005).
Vogelstein et al., *Trends Genet.*, 9(4), 138-141 (1993).
Wang et al., *Anti-Cancer Drug Des.*, 8(3), 193-202 (1993).
Wang et al., *Research Communications in Molecular Pathology and Pharmacology*, 89(3): 291-305 (1995).
Weinberg, *Sci. Am.*, 275, 62-70 (1996).
The International Bureau of WIPO, "International Preliminary Report on Patentability," issued in PCT/US2010/058332: 10 pages, mailed on Jun. 14, 2012.
Alberghini et al., *J. Biol Chem*. 34: 30120-30128 (2005).
Cho et al., *Yonsei Med. Journal*, 49: 451-458 (2008).
Covello et al., *Cancer Research*, 65: 2277-2286 (2005).
Eul et al., *FASEB J.*, express article 10.1096/fj.05-4104fje (2005) http://www.fasebj.org/cgi/doi/10.1096/fj.05-4104fje.
Eul et al., *FASEB J.*, 20: 163-165 (2006).
Franovic, et al., *PNAS*, 106 (50): 21306-21311 (2009).
Ghosh et al., *PNAS*, 105: 12028-12033 (2008).
Gueven et al., *Free Radical Biol Med.*, 41: 992-1000 (2006).
Hyodo et al., *Cancer Research*, 66 (20): 9921-9928 (2006).
International Search Report and Written Opinion of the ISA/EPO of PCT/US2010/058332, 15 pages, mailed Jan. 31, 2011.
Kaelin, Jr., William G., *Clin. Cancer Research*, 10: 6290s-6295s (2004).
Kirkwood et al., *Journal of Clinical Oncology*, 27 (16): 2583-2585 (2009).
Kondo et al., *PLOS Biology*, 1: 439-444 (2003).
Li et al., *Mol. Cell. Biol.*, 27: 5381-5392 (2007).
Lidgren et al., *Clinical Cancer Research*, 11: 1129-1135 (2005).
Linehan et al., *JAMA*, 273 (7): 564-570 (1995).
Linehan, W. et al., *Federal Register*, vol. 75, No. 166 http://edocket.access.gpo.gov/2010/pdf/2010-21349.pdf>, 52758-52760 (2010).
Mahajan et al., *Carcinogenesis*, 29: 1734-1741 (2008).
Maranchie et al., *Cancer Research*, 65: 9190-9193 (2005).
Sabatino et al., *J. Clin Oncol.*, 27: 2645-2652 (2009).
Soule et al., *Free Radical Biol Med.*, 42: 1632-1650 (2007).

\* cited by examiner

NITROXIDE THERAPY FOR THE TREATMENT OF VON HIPPEL—LINDAU DISEASE (VHL) AND RENAL CLEAR CELL CARCINOMA (RCC)

CROSS-REFERENCE TO RELATED APPLICATIONS

This application is a national phase application under 35 U.S.C. §371 of International Application No. PCT/US2010/058332, filed on Nov. 30, 2010, which claims the benefit of U.S. Provisional Patent Application No. 61/265,194, filed on Nov. 30, 2009, all of which are specifically incorporated by reference herein in their entirety.

BACKGROUND OF THE INVENTION

Various disorders, including inherited von Hippel-Lindau (VHL) disease, are associated with elevated expression of HIF-2α. Inherited VHL disease is a cancer syndrome caused by germ line mutations of the VHL tumor suppressor gene. VHL is characterized by angiomas and hemangioblastomas of the brain, spinal cord, and retina. These can lead to cysts and/or tumors of the kidney, pancreas, and adrenal glands (e.g., pheochromocytoma and endolymphatic sac tumors). Renal clear cell carcinoma (RCC) develops in approximately 75% of VHL patients by age 60 and is a leading cause of death in this population. Biallelic loss of VHL gene function is also associated with greater than 60% of all RCC (including sporadic cases). Maranchie et al., *Cancer Res.*, 15: 9190-93 (2005). Thus, subjects with compromised VHL function represent a significant population that has or is at risk for developing cancer, including RCC.

RCC is the most common type of kidney cancer. It is highly resistant to chemotherapy, and the primary treatment for RCC depends largely on surgical removal of cancerous tissue. One current treatment regimen for advanced RCC includes immunotherapy with interleukin-2 (IL-2), although an IL-2 response is seen in less than 20% of patients with advanced RCC. Sabatino et al., *J. Clin. Oncol.*, 27: 2645-52 (2009); Kirkwood et al., *J. Clin. Oncol.*, 27: 2583-2585 (2009). Additional therapeutic agents for advanced RCC include sorafenib, sunitinib maleate, temsirolimus, and everolimus, though there are few complete responses to these agents in patients with advanced RCC. Many RCC patients are asymptomatic and therefore their RCC can go undetected, for example, until revealed by an unrelated imaging procedure. The median survival rate for untreated, metastatic RCC is 12 months, and the 5-year survival rate is less than 10%. Cho et al., *Yonsei Med. J.*, 49: 451-458 (2008).

There is a desire for new molecular therapies that can be used with diseases associated with increased expression of HIF-2α, including VHL disease and sporadic RCC.

BRIEF SUMMARY OF THE INVENTION

The invention provides a method of reducing hypoxia-inducible transcription factor HIF-2α in a subject that has, is suspected to have, or is at risk for having a condition associated with an elevated level of HIF-2α. The method includes administering an effective amount of a stable nitroxide composition to the subject and thereby reducing the level of HIF-2α in the subject.

The invention also provides a method of treating a subject that has, is suspected to have, or is at risk for having von Hippel-Lindau (VHL) disease or renal clear cell carcinoma (RCC). The method of treatment includes administering an effective amount of a stable nitroxide composition to the subject and thereby treating the subject for VHL disease or RCC. Subjects for treatment can be identified, for example, by determining that a sample or biopsy from the subject has a deleterious mutation in at least one allele of the VHL gene.

Additionally, the invention provides a stable nitroxide for use in the manufacture of a medicament or food composition. The medicament or food composition can be for reducing HIF-2α in a subject that has, is suspected to have, or is at risk for having a condition associated with an elevated level of HIF-2α. Thus, the invention provides a stable nitroxide for the treatment of a condition associated with an elevated level of HIF-2α. The medicament or food composition can also be for treating a subject that has, is suspected to have, or is at risk for having von Hippel-Lindau (VHL) disease or renal clear cell carcinoma RCC, wherein a sample or biopsy from the subject has a deleterious mutation in at least one allele of the VHL gene. Thus, the invention provides a stable nitroxide for the treatment of VHL disease or RCC.

An exemplary stable nitroxide for use in the invention is 4-hydroxy-2,2,6,6-tetramethylpiperidine-1-oxyl (Tempol).

DETAILED DESCRIPTION OF THE INVENTION

Figure 1:
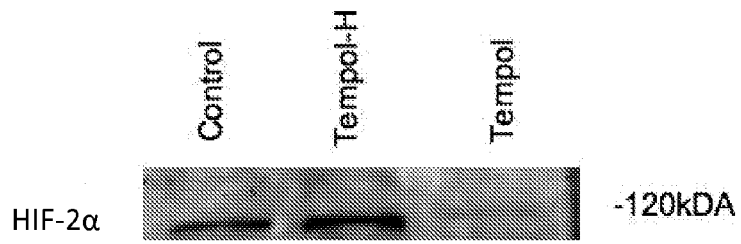
FIG. 1 is a Western blot image depicting HIF-2α levels in nuclear proteins from VHL (−/−) tumor cells treated with growth media (Control), Tempol-H, or Tempol.

The VHL gene product participates in an E3 ubiquitin ligase complex that down regulates an array of genes that promote tumor growth and survival. VHL-regulated genes include VEGF, TGF-α, erythropoietin, and members of the hypoxia-inducible transcription factor (HIF-α) gene family. VHL inactivation results in the accumulation of the proteins encoded by these genes. HIF-α has three homologues HIF-1α, HIF-2α, and HIF-3α. Studies evaluating VHL and the downstream role of HIF-α family members have indicated that several phenotypes associated loss of VHL function, including renal clear cell carcinoma (RCC) tumor growth, require HIF-2α. Li et al., *Mol. Cell. Biol.*, 27: 5381-5392 (2007).

The invention is based, at least in part, on the unexpected discovery that a stable nitroxide can effectively reduce the level of hypoxia-inducible transcription factor HIF-2α. As such, the invention provides a method of reducing HIF-2α expression by administering a stable nitroxide to a subject that has, is suspected to have, or is at risk for having a condition associated with elevated HIF-2α expression. Such conditions include, but are not limited to, conditions associated with elevated HIF-2α due to compromised VHL function.

The invention provides a method for treating a subject that has, is suspected to have, or is at risk for having a condition associated with compromised VHL function, wherein the treatment includes administering an effective amount of a stable nitroxide composition to the subject. Conditions associated with elevated HIF-2α or compromised VHL function include, for example, sporadic RCC, inherited von Hippel-Lindau (VHL) disease, and sporadic VHL disease. Thus, the method can include administering a stable nitroxide to a subject that has, is suspected to have, or is at risk for having a cyst or tumor of the kidney (e.g., RCC), pancreas, or adrenal glands (e.g., pheochromocytoma and endolymphatic sac tumors) due to sporadic or inherited VHL disease. The method also can include administering a stable nitroxide to a subject that has, is suspected to have, or is at risk for an angioma or hemangioblastoma of the brain, spinal cord, or retina due to sporadic or inherited VHL disease.

The method can further include determining that the subject has compromised VHL function, for example, by detecting a deleterious mutation in the VHL gene or a by detecting a reduced level of VHL gene product (mRNA or protein) in a sample or biopsy from the subject, and administering an effective amount of a stable nitroxide composition to the subject.

The invention provides a method for treating a subject that has, is suspected to have, or is at risk for having a condition associated with an elevated level of HIF-2α, wherein the treatment includes administering an effective amount of a stable nitroxide composition to the subject to reduce the level of HIF-2α in the subject. An exemplary condition associated with an elevated level of HIF-2α is the remodeling of pulmonary vasculature due to prolonged alveolar hypoxia. Eul et al., *FASEB J.*, 20: 163-165 (2006). Such hypoxia can occur, e.g., at high altitude in subjects suffering from chronic obstructive pulmonary disease or another restrictive lung disease. The remodeling is characterized by the proliferation and migration of pulmonary artery adventitial fibroblasts and can lead to pulmonary arterial hypertension and cor pulmonale in the subject. Thus, the method can include administering a stable nitroxide composition to a subject that has, is suspected to have, or is at risk for having (a) vascular remodeling of the lungs due to prolonged alveolar hypoxia, (b) pulmonary arterial hypertension, and/or (c) cor pulmonale. The method can further include determining that the subject has an elevated level of HIF-2α gene product (mRNA or protein), in addition to administering an effective amount of a stable nitroxide composition to the subject.

As used herein, the terms "treat," "treating," and "treatment" refer to both preventive and ameliorative treatment. Thus, in the therapeutic methods of the invention, the administration of a stable nitroxide composition can contribute to an overall rational medical approach that diminishes the incidence of (e.g., inhibits tumor formation or vascular remodeling) and/or the mortality associated with VHL disease, RCC, or a condition associated with elevated level of HIF-2α. Furthermore, the terms "treat," "treating," and "treatment" do not necessarily imply 100% or complete treatment. Rather, there are varying degrees of treatment, which one of ordinary skill in the art recognizes as having a potential benefit or therapeutic effect. In this respect, the methods of the invention can provide any amount or any level of treatment and the methods of treatment provided can include the treatment of one or more conditions or symptoms of the disease being treated. For example, the methods of the invention can reduce the symptoms associated with (i) growth or persistence of cysts or tumors associated with a reduction or loss of VHL function or (ii) the vascular remodeling, pulmonary hypertension, or cor pulmonale associated with elevated HIF-2α expression.

The term "subject," as used herein refers to an animal, e.g., preferably, a mammal and, more preferably, a human. Animal subjects include, but are not limited to dogs, cats, horses, cows, pigs, sheep, goats, birds, fish and the like, as well as mammalian models of conditions or disorders associated with compromised VHL function and/or elevated HIF-2α, such as, e.g., sporadic VHL disease, inherited VHL disease, sporadic RCC, prolonged hypoxia, pulmonary arterial hypertension, and cor pulmonale.

In certain embodiments of the invention, the stable nitroxide is administered to a subject with compromised VHL function. Compromised VHL function can be due to a deleterious mutation in one or two alleles of the VHL gene. Such mutations can be inherited or they can be somatic (e.g., spontaneous or induced) mutations that arise during the subject's lifetime. As used herein deleterious mutations include insertions, deletions, translocations, nonsense mutations, and missense mutations that reduce the expression or compromise the function of the VHL gene product. Any suitable method can be used to determine whether a subject has a deleterious mutation in the VHL gene. For example, a sample or biopsy from the subject can be evaluated for a deleterious mutations in the VHL gene, e.g., by polymerase chain reaction (PCR) amplification, allele-specific PCR, Southern blot, or DNA sequencing. Compromised VHL function can also be identified by detecting a reduced level of the VHL gene product (e.g., reduced mRNA or protein level) in a sample or biopsy from the subject. As used herein, a reduced level of VHL gene product refers to a level that is significantly lower than expected, e.g., as compared to a control level of VHL gene product. The control level can be the level or average of levels of VHL gene product detected in one or more samples or biopsies taken from the subject at an earlier time, i.e., before the sample or biopsy with a reduced level is taken. Alternatively, the control level can be the level or the average of levels of VHL gene product detected in one or more samples or biopsies taken from one or more healthy subjects that lack a deleterious mutation in the VHL gene, do not suffer from compromised VHL function, and/or do not suffer from elevated HIF-2α. A sample or biopsy with a reduced level of VHL gene product can have, for example, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, or about 10% or less VHL gene product relative to a control level of VHL gene product. The reduced level and control level are preferably determined using the same or comparable techniques to detect the levels of VHL gene product in samples or biopsies from equivalent anatomical regions or tissue sources.

In some embodiments of the invention, the subject has an elevated level of HIF-2α gene product (e.g., elevated mRNA or protein level). As used herein, an elevated or higher level of HIF-2α gene product refers to an amount of gene product in a sample or biopsy from the subject that is significantly higher than expected, e.g., as compared to a control level of HIF-2α gene product. The control level can be the level or average of levels of HIF-2α gene product detected in one or more samples or biopsies taken from the subject at an earlier time, i.e., before the sample or biopsy with elevated HIF-2α is taken. Alternatively, the control level can be the level or the average of levels of HIF-2α gene product detected in one or more samples or biopsies taken from one or more healthy subjects that do not suffer from a condition associated with an elevated level of HIF-2α. A sample or biopsy with an elevated level of HIF-2α gene product can have, for example, about 10% or more, about 20% or more, about 30% or more, about 40% or more, about 50% or more, about 60% or more, about 70% or more, about 80% or more, about 90% or more, about 100% or more, about 150% or more, about 200% or more, about 250% or more, about 300% or more, about 400% or more, or about 500% or more of the HIF-2α gene product in excess of a control level of HIF-2α gene product. The elevated level and control level are preferably determined using the same or comparable techniques to detect the levels of HIF-2α gene product in samples or biopsies from equivalent anatomical regions or tissue sources.

Techniques for determining the level of a gene (e.g., VHL or HIF-2α) product can include, for example, techniques such as Western blot, dot blot, immunoassay, enzyme-linked immunosorbent assay (ELISA), fluorescent in-situ hybridization (FISH), real-time reverse transcription-polymerase chain reaction (real time RT-PCR), Northern blot, and "gene chip" or microarray expression analysis.

Stable nitroxide compositions that can be used in the methods of the invention can include any stable nitroxide suitable for administering to a subject. A stable nitroxide composition can include, for example, piperidine nitroxide derivatives such as 4-hydroxy-2,2,6,6-tetramethylpiperidine-1-oxyl (Tempol); 2,2,6,6-tetramethylpiperidine-1-oxyl (Tempo); 4-amino-2,2,6,6-tetramethyl-1-piperidinyloxy (Tempamine); and 4-oxo-2,2,6,6-tetramethyl-1-piperidinyloxy (4-oxo-Tempo). Stable nitroxide compositions can also include other substituted variants of Tempo (typically in the 4 position) such as, for example, 4-(2-bromoacetamido)-2,2,6,6-tetramethylpiperidine-1-oxyl; 4-ethoxyfluorophosphonyloxy-2,2,6,6-tetramethylpiperidine-1-oxyl; 4-(2-iodoacetamido)-2,2,6,6-tetramethylpiperidine-1-oxyl, 4-isothiocyanato-2,2,6,6-tetramethylpiperidine-1-oxyl; 4-maleimido-2,2,6,6-tetramethylpiperidine-1-oxyl; 4-(4-nitrobenzoyloxyl)-2,2,6,6-tetramethylpiperidine-1-oxyl; 4-phosphonooxy-2,2,6,6-tetramethylpiperidine-1-oxyl; and the like.

Other suitable stable nitroxide compounds include 2-ethyl-2,5,5-trimethyl-3-oxazolidine-1-oxyl (Oxano); 3-aminomethyl-2,2,5,5-tetramethyl-1-pyrrolidinyl-N-oxyl (3-aminomethyl-Proxyl); 3-cyano-2,2,5,5-tetramethyl-1-pyrrolidinyl-N-oxyl(3-cyano-Proxyl); 3-Carbamoyl-2,2,5,5-tetramethyl-1-pyrrolidinyl-N-oxyl (3-Carbamoyl-Proxyl); and 3-Carboxy-2,2,5,5-tetramethyl-1-pyrrolidinyl-N-oxyl (3-Carboxy-Proxyl).

The effective amount (i.e., dose) of stable nitroxide (e.g., Tempol) to be administered to a subject can be determined depending upon, for example, age, body weight, symptom, the desired therapeutic effect, the route of administration, and the duration of the treatment. Exemplary doses can be from about 0.01 to about 1000 mg, by oral administration. Exemplary dose ranges can include from a minimum dose of about 0.01, 0.10, 0.50, 1, 5, 10, 25, 50, 100, 125, 150, 200, or 250 mg to a maximum dose of about 300, 400, 500, 600, 700, 800, 900, or 1000 mg, wherein an exemplary dose range can include from any one of the foregoing minimum doses to any one of the foregoing maximum doses. Specific examples of particular effective amounts contemplated via oral administration include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, 1000 mg or more. The oral dose can be administered once daily, twice daily, three times daily, or more frequently.

The dose of stable nitroxide (e.g., Tempol) for use in parenteral administration (preferably intravenous administration) is generally from about 0.01 to about 300 mg/kg body weight. Exemplary dose ranges can include from a minimum dose of about 0.01, 0.10, 0.50, 1, 5, 10, 25, 50, or 100 mg/kg body weight to a maximum dose of about 125, 150, 175, 200, 250, 275, or 300 mg/kg body weight, wherein an exemplary dose range can include from any one of the foregoing minimum doses to any one of the foregoing maximum doses. Specific examples of particular effective amounts contemplated include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300 mg/kg body weight or more. Continuous intravenous administration is also contemplated for from 1 to 24 hours per day to achieve a target concentration from about 0.01 mg/L blood to about 100 mg/L blood. Exemplary dose ranges can include from a minimum dose of about 0.01, 0.10, 0.25, 0.50, 1, 5, 10, or 25 mg/L blood to a maximum dose of about 40, 45, 50, 55, 60, 65, 70, 75, 80, 85, 90, or 100 mg/L, wherein an exemplary dose range can include from any one of the foregoing minimum doses to any one of the foregoing maximum doses. Specific examples of particular effective amounts contemplated via this route include about 0.02, 0.03, 0.04, 0.05, 0.10, 0.15, 0.20, 0.25, 0.30, 0.35, 0.40, 0.45, 0.50, 0.55, 0.60, 0.65, 0.70, 0.75, 0.80, 0.85, 0.90, 0.95, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg/L blood or more. The dose to be used can depend upon various conditions, and there may be cases wherein doses lower than or greater than the ranges specified above are used.

The stable nitroxide (e.g., Tempol) may be administered in the form of, for example, solid compositions, liquid compositions, or other compositions for oral administration, injections, liniments, or suppositories for parenteral administration. Solid compositions for oral administration include compressed tablets, pills, capsules, dispersible powders, and granules. Capsules include hard capsules and soft capsules. In such solid compositions, the stable nitroxide can be admixed with an excipient (e.g., lactose, mannitol, glucose, microcrystalline cellulose, or starch), combining agents (e.g., hydroxypropyl cellulose, polyvinyl pyrrolidone, or magnesium metasilicate aluminate), disintegrating agents (e.g., cellulose calcium glycolate), lubricating agents (e.g., magnesium stearate), stabilizing agents, agents to assist dissolution (e.g., glutamic acid or aspartic acid), or the like. The agents may, if desired, be coated with coating agents (e.g., sugar, gelatin, hydroxypropyl cellulose, or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups, and elixirs. In such compositions, the stable nitroxide is dissolved, suspended, or emulsified in a commonly used diluent (e.g. purified water, ethanol, or mixture thereof). Furthermore, such liquid compositions may also comprise wetting agents, suspending agents, emulsifying agents, flavoring agents (e.g., flavor-masking agents) sweetening agents, perfuming agents, preserving agents, buffer agents, or the like.

Injections for parenteral administration include solutions, suspensions, emulsions, and solids which are dissolved or suspended. For injections, the stable nitroxide can be dissolved, suspended, and/or emulsified in a solvent. The solvents are, for example, distilled water for injection, physiological salt solution, vegetable oil, propylene glycol, polyethylene glycol, alcohol such as ethanol, or a mixture thereof. Moreover the injections also can include stabilizing agents, agents to assist dissolution (e.g., glutamic acid, aspartic acid, or POLYSORBATE 80™), suspending agents, emulsifying agents, soothing agents, buffer agents, preserving agents, etc. The compositions are sterilized in the final process or manufactured and prepared by sterile procedure. The compositions also can be manufactured in the form of sterile solid compositions, such as a freeze-dried composition, and can be sterilized or dissolved immediately before use in sterile distilled water for injection or some other solvent.

Other compositions for parenteral administration include liquids and ointments for external use, endermic liniments, compositions for inhalation, sprays, suppositories for rectal administration, and pessaries for vaginal administration, which compositions include a stable nitroxide and are administered by methods known in the art.

Stable nitroxide compositions for inhalation or sprays may comprise additional substances other than diluents, such as, e.g., stabilizing agents (e.g. sodium sulfite hydride), isotonic buffers (e.g. sodium chloride, sodium citrate or citric acid). See, for example, the methods described in U.S. Pat. Nos. 2,868,691 and 3,095,355. The nitroxide can be effectively distributed by inhalation or spray using a self-propelling composition that includes a solution or dispersion of the stable nitroxide in micronized form. For example, an effective dispersion of finely divided drug particles can be accomplished with the use of very small quantities of a suspending agent, present as a coating on micronized drug particles. Evaporation of the propellant from the aerosol particles after spraying from the aerosol container leaves finely divided drug particles coated with a fine film of the suspending agent. In the micronized form, the average particle size can be less than about 5 microns. The propellant composition can employ, as the suspending agent, a fatty alcohol such as oleyl alcohol. Propellants that may be employed include hydrofluoroalkane propellants and chlorofluorocarbon propellants. Dry powder inhalation also can be employed.

Stable nitroxide compositions suitable for inhalation may be used, for example, in a method of the invention to treat or reduce the remodeling of the pulmonary vasculature associated with prolonged alveolar hypoxia, e.g., in subjects that have, are suspected to have, or are at risk for pulmonary arterial hypertension, and cor pulmonale.

In some embodiments, the stable nitroxide (e.g., Tempol) can be administered as a supplement with food or drink. Thus, the stable nitroxide can be mixed into a food or drink composition, which, optionally, masks the flavor of the nitroxide.

The following examples further illustrate the invention but, of course, should not be construed as in any way limiting its scope.

EXAMPLE 1

This example demonstrates the use of a stable nitroxide to reduce HIF-2α in VHL-compromised tumor cells.

The human sporadic RCC cell line 786-0 was obtained from the American Tissue Culture Collection (ATCC) (Manassas, Va.). This cell line contains a single inactivated VHL allele, produces no VHL protein, is deficient for HIF-1α expression, and constitutively expresses HIF-2α. Gnarra et al., *Nat. Genet.*, 7: 85-90 (1994) and Maxwell et al., *Nature*, 399: 271-275 (1999). Cultures of 786-0 cells were pre-incubated for one hour in KREB's buffer (115 mM NaCl, 5.9 mM KCl, 1.2 mM $MgCl_2$, 1.2 mM $NaH_2PO_4$, 1.2 mM $Na_2SO_4$, 2.5 mM $CaCl_2$, and 25 mM $NaHCO_3$) at pH 7.4 and with 4.5 g/L of glucose. Cells were then treated for two to four hours with (i) Tempol (5 mM) obtained from Sigma Aldrich (St. Louis, Mo.), (ii) its non-functional hydroxylamine (protonated, reduced) variant: 1,4-dihydroxy-2,2,6,6-tetramethylpiperidine (Tempol-H) (5 mM) (Sigma Aldrich), or (iii) growth medium as a negative control. Cells were harvested, nuclear protein extractions performed, and protein concentrations were measured by BCA assay from Pierce (Rockford, Ill.). Aliquots of extracted nuclear proteins (20 µg) were loaded in a 7.5% polyacrylamide gel and separated by sodium dodecyl sulfate polyacrylamide gel electrophoresis (SDS-PAGE). Proteins were transferred to PVDF membranes, which were then blocked for one to sixteen hours in a solution of 5% dry milk. Blocked membranes were incubated with a primary antibody overnight at a dilution 1:1000. Primary HIF-2α antibody was from Novus Biologicals, LLC (Littleton, Colo.) or R&D Systems (Minneapolis, Minn.). Primary HIF-1α antibody was from the BD TRANSDUCTION line sold by BD Bioscience (San Jose, Calif.). Membranes were subsequently incubated with secondary antibodies for two to four hours at room temperature and visualized using ECL chemiluminescence detection reagents from Amersham Biosciences (Piscataway, N.J.) and exposing to x-ray film.

The resulting x-ray image of a western blot probed with HIF-2α antibody is depicted in FIG. 1. FIG. 1 shows that HIF-2α levels were significantly reduced in Tempol-treated RCC cells as compared to those treated with Tempol-H or growth medium (control). Additionally, eight other cell lines from patients with VHL mutations were examined. In each of these patient cell lines, Tempol treatment reduced HIF2 α levels significantly.

The foregoing demonstrates that treatment with a stable nitroxide effectively inhibited expression of HIF-2α in cultured tumor cells lacking VHL.

EXAMPLE 2

This example demonstrates the use of a stable nitroxide to inhibit VHL-compromised tumors in mammals.

The tumor inhibitory effect of stable nitroxides were studied in vivo using mice with mutations in the Prkdc gene (SCID, which is associated severe combined immunodeficiency), and bg (BEIGE) gene. Twenty female SCID/BEIGE mice (C.B-Igh-1b/GbmsTac-Prkdc$^{scid}$-Lyst$^{bg}$ N7 (CBSCBG) from Taconic (Hudson, N.Y.)) were injected with about 8 million 786-0 (VHL-/-) cells subcutaneously on the right flank. Starting on the day of injection, Tempol was diluted in PBS and added twice a week to the water bottle feeding a group of ten injected mice. The final concentration of Tempol in water was 2 mM. The control group of ten remaining mice received an equivalent amount of PBS in water twice a week. The volume of the tumors and weight of the mice were recorded once a week for up to 100 days. When the control group tumor volume reached 1 cm$^3$, tumors of 8 mice maintained as controls were harvested. At the same time, 4 of the animals maintained on Tempol were harvested and fast-frozen or paraffin embedded for further experiments. The average tumor volume as a function of time for each group is depicted in FIG. 2.

Figure 2:
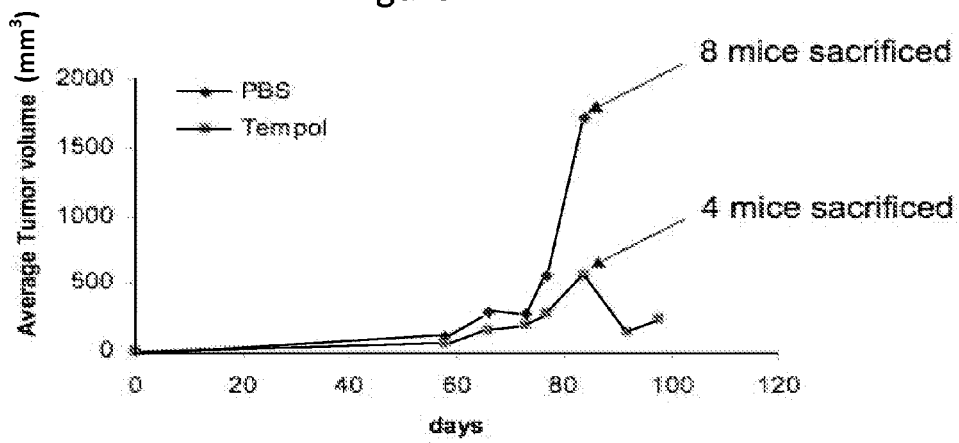
FIG. 2 is a graph depicting average VHL (−/−) tumor volume ($mm^3$) versus time in mice treated with water supplemented with PBS or Tempol.

As shown in FIG. 2, tumors grew faster in control animals not administered Tempol. By contrast, mice maintained on Tempol had smaller tumors when sacrificed at the 80 day time point. Furthermore, four animals maintained on Tempol had small tumors that did not require sacrificing them, and these mice were maintained up to 100 days. Notably the tumors of these four mice were quite small, even at 100 days. Thus, the results depicted in FIG. 2 indicate that the group of mice administered Tempol had a markedly lower average tumor volume as compared to the control group.

The foregoing provides in vivo confirmation that administration of a stable nitroxide solution can be used to treat and prevent the growth of tumors with reduced VHL gene product in mammals.

EXAMPLE 3

This example further demonstrates the use of a stable nitroxide to inhibit VHL-compromised tumors in a mammal.

Figure 3:
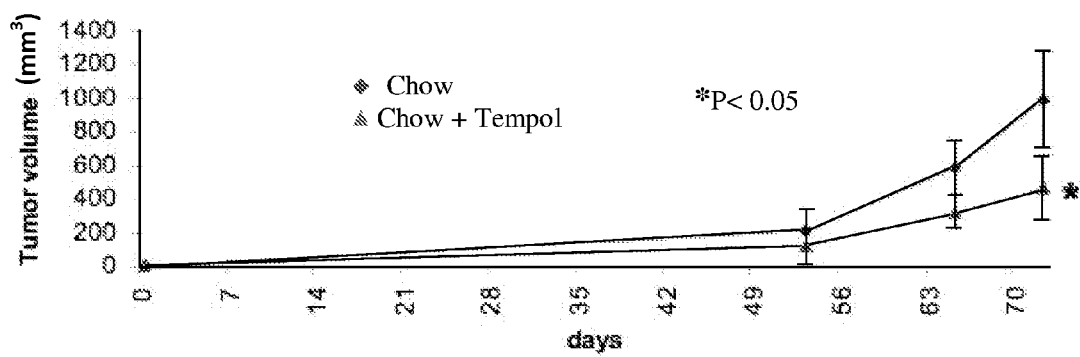
FIG. 3 is a graph depicting VHL (−/−) tumor volumes ($mm^3$) versus time in mice treated with standard chow or chow supplemented with Tempol.

Twenty female SCID/BEIGE mice were injected with 786-0 cells (VHL−/−) subcutaneously on the right flank, as described in Example 2. Starting on the day of injection, a control group of ten injected mice were fed standard chow (NIH-031, Zeigler Brothers, Inc. (Gardners, Pa.)) and a group ten injected mice received chow supplemented with Tempol. The Tempol diet supplement was made by a cold press technique from powdered Tempol uniformly mixed with bacon-flavored mouse chow (Bio-Serv Inc. (Frenchtown, N.J.)) providing a Tempol concentration of 10 mg/g of food. Bacon-flavored chow without Tempol was also added to the control diet. The volume of the tumors and the weight of the mice were recorded once a week for more than ten weeks. Tumor volumes as a function of time are depicted in FIG. 3. When the tumor volumes of the control group reached 1 cm$^3$, the tumors of all mice were harvested and fast-frozen or paraffin embedded for further experiments.

As shown in FIG. 3, after ten weeks, tumor growth was reduced by a statistically significant amount (P<0.05) in mice fed Tempol in their chow, as compared to control group mice fed normal chow.

The foregoing confirms that dietary administration of a stable nitroxide can be used to treat and prevent the growth of tumors lacking functional VHL protein in mammals.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a subject that has von Hippel-Lindau (VHL) disease or renal clear cell carcinoma (RCC), which method comprises:
    (a) determining whether a sample or biopsy from the subject has a deleterious mutation in at least one allele of the VHL gene,
    (b) detecting the level of HIF-2α mRNA or protein in the sample or biopsy, and
    (c) administering an effective amount of a nitroxide composition to the subject if the sample or biopsy from the subject has a deleterious mutation in at least one allele of the VHL gene and an elevated level of HIF-2α mRNA or protein, thereby treating the subject for VHL or RCC.

2. The method of claim 1, wherein the subject has von Hippel-Lindau (VHL) disease.

3. The method of claim 2, wherein the subject has inherited von Hippel-Lindau (VHL) disease.

4. The method of claim 1, wherein the subject has renal clear cell carcinoma (RCC).

5. The method of claim 4, wherein the RCC is sporadic.

6. The method of claim 1, wherein the subject has a deleterious mutation in at least one allele of the VHL gene.

7. The method of claim 1, wherein the subject has a deleterious mutation in two alleles of the VHL gene.

8. The method of claim 2, wherein the subject has a tumor selected from the group consisting of kidney, pancreas, and adrenal gland tumors.

9. The method of claim 2, wherein the subject has an angioma or hemangioblastoma selected from the group consisting of brain, spinal cord, and retinal angiomas or hemangioblastomas.

10. The method of claim 2, wherein the subject has pulmonary arterial hypertension and/or cor pulmonale.

11. The method of claim 1, wherein the stable nitroxide composition comprises a stable nitroxide selected from the group consisting of 2,2,6,6-tetramethylpiperidine-1-oxyl (Tempo), 4-hydroxy-2,2,6,6-tetramethylpiperidine-1-oxyl (Tempol), 4-amino-2,2,6,6-tetramethyl-1-piperidinyloxy (Tempamine), 4-oxo-2,2,6,6-tetramethyl-1-piperidinyloxy (4-oxo-Tempo) 2-ethyl-2,5,5-trimethyl-3-oxazolidine-1-oxyl (Oxano), 3-aminomethyl-2,2,5,5-tetramethyl-1-pyrrolidinyl-N-oxyl (3-aminomethyl-Proxyl), 3-cyano-2,2,5,5-tetramethyl-1-pyrrolidinyl-N-oxyl (3-cyano-Proxyl), 3-Carbamoyl-2,2,5,5-tetramethyl-1-pyrrolidinyl-N-oxyl (3-Carbamoyl-Proxyl), and 3-Carboxy-2,2,5,5-tetramethyl-1-pyrrolidinyl-N-oxyl (3-Carboxy-Proxyl).

12. The method of claim 11, wherein the stable nitroxide is Tempol.

13. The method of claim 1, which comprises detecting the level of HIF-2α mRNA in the sample or biopsy.

14. The method of claim 1, which comprises detecting the level of HIF-2α protein in the sample or biopsy.

15. The method of claim 2, wherein the subject has a deleterious mutation in at least one allele of the VHL gene.

16. The method of claim 2, wherein the subject has a deleterious mutation in two alleles of the VHL gene.

17. The method of claim 2, wherein the stable nitroxide composition comprises a stable nitroxide selected from the group consisting of 2,2,6,6-tetramethylpiperidine-1-oxyl (Tempo), 4-hydroxy-2,2,6,6-tetramethylpiperidine-1-oxyl (Tempol), 4-amino-2,2,6,6-tetramethyl-1-piperidinyloxy (Tempamine), 4-oxo-2,2,6,6-tetramethyl-1-piperidinyloxy (4-oxo-Tempo) 2-ethyl-2,5,5-trimethyl-3-oxazolidine-1-oxyl (Oxano), 3-aminomethyl-2,2,5,5-tetramethyl-1-pyrrolidinyl-N-oxyl (3-aminomethyl-Proxyl), 3-cyano-2,2,5,5-tetramethyl-1-pyrrolidinyl-N-oxyl (3-cyano-Proxyl), 3-Carbamoyl-2,2,5,5-tetramethyl-1-pyrrolidinyl-N-oxyl (3-Carbamoyl-Proxyl), and 3-Carboxy-2,2,5,5-tetramethyl-1-pyrrolidinyl-N-oxyl (3-Carboxy-Proxyl).

18. The method of claim 17, wherein the stable nitroxide is Tempol.

19. The method of claim 3, which comprises detecting the level of HIF-2α mRNA in the sample or biopsy.

20. The method of claim 3 which comprises detecting the level of HIF-2α protein in the sample or biopsy.

21. The method of claim 3, wherein the subject has a deleterious mutation in at least one allele of the VHL gene.

22. The method of claim 3, wherein the subject has a deleterious mutation in two alleles of the VHL gene.

23. The method of claim 3, wherein the stable nitroxide composition comprises a stable nitroxide selected from the group consisting of 2,2,6,6-tetramethylpiperidine-1-oxyl (Tempo), 4-hydroxy-2,2,6,6-tetramethylpiperidine-1-oxyl (Tempol), 4-amino-2,2,6,6-tetramethyl-1-piperidinyloxy (Tempamine), 4-oxo-2,2,6,6-tetramethyl-1-piperidinyloxy (4-oxo-Tempo) 2-ethyl-2,5,5-trimethyl-3-oxazolidine-1-oxyl (Oxano), 3-aminomethyl-2,2,5,5-tetramethyl-1-pyrrolidinyl-N-oxyl (3-aminomethyl-Proxyl), 3-cyano-2,2,5,5-tetramethyl-1-pyrrolidinyl-N-oxyl (3-cyano-Proxyl), 3-Carbamoyl-2,2,5,5-tetramethyl-1-pyrrolidinyl-N-oxyl (3-Carbamoyl-Proxyl), and 3-Carboxy-2,2,5,5-tetramethyl-1-pyrrolidinyl-N-oxyl (3-Carboxy-Proxyl).

24. The method of claim 23, wherein the stable nitroxide is Tempol.

25. The method of claim 4, which comprises detecting the level of HIF-2α mRNA in the sample or biopsy.

26. The method of claim 4, which comprises detecting the level of HIF-2α protein in the sample or biopsy.

27. The method of claim 4, wherein the subject has a deleterious mutation in at least one allele of the VHL gene.

28. The method of claim 4, wherein the subject has a deleterious mutation in two alleles of the VHL gene.

29. The method of claim 4, wherein the stable nitroxide composition comprises a stable nitroxide selected from the group consisting of 2,2,6,6-tetramethylpiperidine-1-oxyl (Tempo), 4-hydroxy-2,2,6,6-tetramethylpiperidine-1-oxyl (Tempol), 4-amino-2,2,6,6-tetramethyl-1-piperidinyloxy (Tempamine), 4-oxo-2,2,6,6-tetramethyl-1-piperidinyloxy (4-oxo-Tempo) 2-ethyl-2,5,5-trimethyl-3-oxazolidine-1-oxyl (Oxano), 3-aminomethyl-2,2,5,5-tetramethyl-1-pyrrolidinyl-N-oxyl (3-aminomethyl-Proxyl), 3-cyano-2,2,5,5-tetramethyl-1-pyrrolidinyl-N-oxyl (3-cyano-Proxyl), 3-Carbamoyl-2,2,5,5-tetramethyl-1-pyrrolidinyl-N-oxyl (3-Carbamoyl-Proxyl), and 3-Carboxy-2,2,5,5-tetramethyl-1-pyrrolidinyl-N-oxyl (3-Carboxy-Proxyl).

30. The method of claim 29, wherein the stable nitroxide is Tempol.

31. The method of claim 5, which comprises detecting the level of HIF-2α mRNA in the sample or biopsy.

32. The method of claim 5, which comprises detecting the level of HIF-2α protein in the sample or biopsy.

33. The method of claim 5, wherein the subject has a deleterious mutation in at least one allele of the VHL gene.

34. The method of claim 5, wherein the subject has a deleterious mutation in two alleles of the VHL gene.

35. The method of claim 5, wherein the stable nitroxide composition comprises a stable nitroxide selected from the group consisting of 2,2,6,6-tetramethylpiperidine-1-oxyl (Tempo), 4-hydroxy-2,2,6,6-tetramethylpiperidine-1-oxyl (Tempol), 4-amino-2,2,6,6-tetramethyl-1-piperidinyloxy (Tempamine), 4-oxo-2,2,6,6-tetramethyl-1-piperidinyloxy (4-oxo-Tempo) 2-ethyl-2,5,5-trimethyl-3-oxazolidine-1-oxyl (Oxano), 3-aminomethyl-2,2,5,5-tetramethyl-1-pyrrolidinyl-N-oxyl (3-aminomethyl-Proxyl), 3-cyano-2,2,5,5-tetramethyl-1-pyrrolidinyl-N-oxyl (3-cyano-Proxyl), 3-Carbamoyl-2,2,5,5-tetramethyl-1-pyrrolidinyl-N-oxyl (3-Carbamoyl-Proxyl), and 3-Carboxy-2,2,5,5-tetramethyl-1-pyrrolidinyl-N-oxyl (3-Carboxy-Proxyl).

36. The method of claim 35, wherein the stable nitroxide is Tempol.

\* \* \* \* \*